United States Patent [19]

Dusza et al.

[11] Patent Number: 5,059,691

[45] Date of Patent: Oct. 22, 1991

[54] N-((DIALKYLAMINO)METHYLENE)-SUBSTITUTED PYRAZOLO (1,5-A)-PYRIMIDINE-3-CARBOXAMIDES AND N-((DIALKYLAMINO)METHYLENE)-SUBSTITUTED-4,5-DIHYDROPYRAZOLO-(1,5-A)-PYRIMIDINE-3-CARBOXAMIDES

[75] Inventors: John P. Dusza, Nanuet, N.Y.; Shin S. Tseng, Bridgewater, N.J.

[73] Assignee: American Cyanamid Company, Stamford, Conn.

[21] Appl. No.: 468,449

[22] Filed: Jan. 22, 1990

[51] Int. Cl.$^5$ ............................................. C07D 471/02
[52] U.S. Cl. .................................................... 544/281
[58] Field of Search .......................... 544/281; 514/258

[56] References Cited

U.S. PATENT DOCUMENTS 4,178,449 12/1979 Dusza et al. ..................... 544/281
4,576,943 3/1986 Tomcufcik et al. ................ 544/159

Primary Examiner—Mukund J. Shah
Assistant Examiner—Jyothsna Venkat
Attorney, Agent, or Firm—H. G. Jackson

[57] ABSTRACT

Novel N-((dialkylamino)methylene)-substituted-pyrazolo(1,5-a)pyrimidine-3-carboxamide and N-((dialkylamino))methylene-substituted-4,5-dihydropyrazolo-(1,5-a)-pyrimidine-3-carboxamide compounds are disclosed which are useful as neurotropic and/or anxiolytic and/or anti-hypertensive agents in mammals.

9 Claims, No Drawings

N-((DIALKYLAMINO)METHYLENE)-SUBSTITUTED PYRAZOLO (1,5-A)-PYRIMIDINE-3-CARBOXAMIDES AND N-((DIALKYLAMINO)METHYLENE)-SUBSTITUTED-4,5-DIHYDROPYRAZOLO-(1,5-A)-PYRIMIDINE-3-CARBOXAMIDES

The present invention relates to new organic compounds and more particularly it relates to novel N-((dialkylamino)methylene)-substituted-pyrazolo-(1,5-a)pyrimidine-3-carboxamide and to N-((dialkylamino)methylene)-substituted-4,5-dihydropyrazolo-(1,5-a)-pyrimidine-3-carboxamide compounds which are useful as neurotropic agents, anxiolytic agents and/or antihypertensive agents in mammals.

BACKGROUND OF THE INVENTION

Various medicinal agents have been employed in the treatment of persons suffering from nervousness, anxiety and hypertension, as well as cognitive disorders.

Denzel et al, U.S. Pat. No. 4,072,681, discloses 3,7-dihydro- and 1,7-dihydro-4H-pyrazolo (4',3':5,6)pyrido(4,3-d)pyrimidin-4-ones which have the general formula (I):

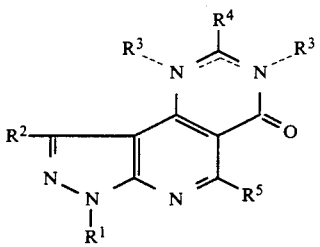

wherein $R^1$ is hydrogen, lower alkyl or phenyl; $R^2$, $R^4$ and $R^5$ each is hydrogen or lower alkyl; and $R^3$ is hydrogen, lower alkyl, phenyl, substituted phenyl, phenyl-lower alkyl or di(lower alkyl)-amino-lower alkyl. These compounds are said to exhibit both anti-inflammatory properties and central nervous system depressant activity.

Dusza et al, U.S. Pat. No. 4,281,000 discloses substituted pyrazolo(1,5-a)pyrimidines of the general formula (II):

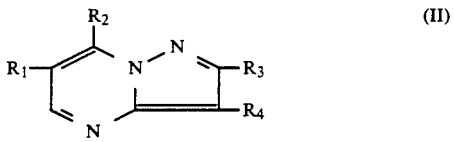

wherein $R_1$ is hydrogen or alkyl having from 1 to 3 carbon atoms; $R_2$ is selected from the group consisting of

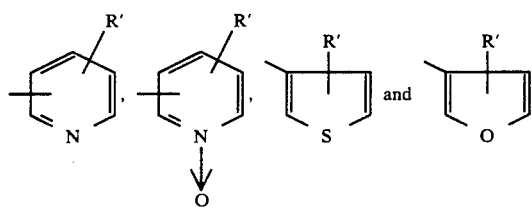

wherein R' is hydrogen or alkyl having from 1 to 3 carbon atoms; $R_3$ is hydrogen, fluoro, chloro, bromo, cyano, cyanomethyl, carbamoyl or alkyl having from 1 to 3 carbons atoms; and $R_4$ is selected from the group consisting of hydrogen, fluoro, chloro, bromo, formyl, carboxyl, cyano, hydroxymethyl, N-hydroxyformimidoyl, alkyl having from 1 to 3 carbon atoms and moieties of the formulae:

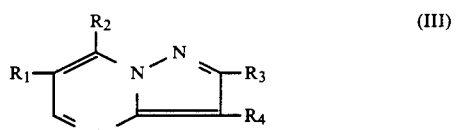

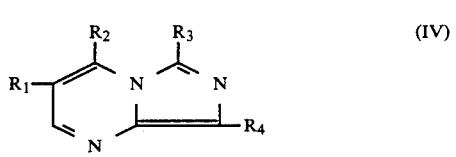

where R is alkyl having from 1 to 3 carbon atoms. The disclosed compounds are said to exhibit anxiolytic activity.

Dusza et al, U.S. Pat. No. 4,178,449 discloses substituted pyrazolo(1,5-a) pyrimidines and imidazo(1,5-a) pyrimidines of the general formulae (III) and (IV) respectively:

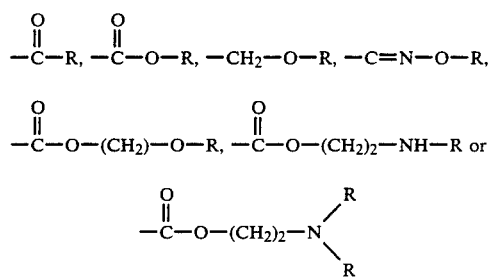

wherein $R_1$ is hydrogen or alkyl having from 1 to 3 carbon atoms; $R_2$ is selected from the group consisting of phenyl, ortho-trifluoromethylphenyl, meta-trifluoromethylphenyl and meta-methoxyphenyl; $R_3$ is hydrogen, fluoro, chloro, bromo, cyano, cyanomethyl, carbamoyl or alkyl having from 1 to 3 carbon atoms; and $R_4$ is selected from the group consisting of hydrogen, fluoro, chloro, bromo, formyl, carboxyl, cyano, hydroxymethyl, N-hydroformimidoyl, alkyl having from 1 to 3 carbon atoms and moieties of the formulae:

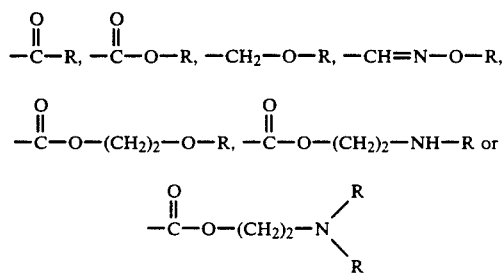

where R is alkyl having from 1 to 3 carbon atoms.

SUMMARY OF THE INVENTION

The present invention relates to new organic compounds and more particularly is concerned with N-((dialkylamino)methylene)substituted pyrazolo(1,5-a)pyrimidine-3-carboxamides and N-((dialkylamino)methylene)substituted-4,5-dihydropyrazolo(1,5-a)pyrimidine-3-carboxamides useful as neurotropic agents, anxiolytic agents and/or antihypertensive agents in mammals. The compounds of the present invention may be represented by the following structural formula:

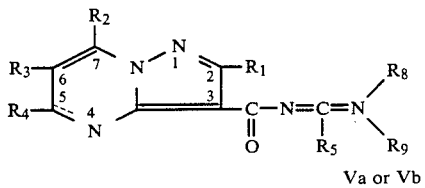

Va or Vb wherein --- may represent the presence of a double bond between the $N^4$ and $C^5$ position, Va, or the absence of a double bond between the $N^4$ and $C^5$ position and a hydrogen atom bonded to the $N^4$ position, Vb; $R_1$, $R_3$, $R_4$ and $R_5$ may be the same or different and are selected from hydrogen or $C_1$ to $C_3$ alkyl and $R_2$ is selected from the group consisting of hydrogen, 3-pyridinyl, 4-pyridinyl and

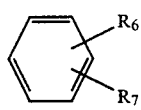

(where $R_6$ and $R_7$ may be the same or different and are selected from the group consisting essentially of hydrogen, halogen, $C_1$ to $C_3$ alkyl and trifluoromethyl), $R_8$ and $R_9$ may be the same or different and are selected from $C_1$ to $C_3$ alkyl and where halogen is selected from chlorine, bromine and fluorine.

A preferred embodiment of the present invention may be represented by the following structural formula:

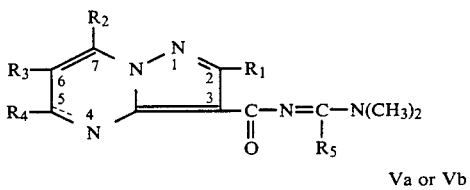

Va or Vb wherein --- may represent the presence of a double bond between the $N^4$ and $C^5$ position, Va, or the absence of a double bond between the $N^4$ and $C^5$ position and a hydrogen atom bonded to the $N^4$ position, Vb; $R_1$, $R_3$, $R_4$ and $R_5$ may be the same or different and are selected from hydrogen or $C_1$ to $C_3$ alkyl and $R_2$ is selected from the group consisting of hydrogen, 3-pyridinyl, 4-pyridinyl and

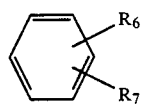

(wherein $R_6$ and $R_7$ may be the same or different and are selected from the group consisting essentially of hydrogen, halogen, $C_1$ to $C_3$ alkyl and trifluoromethyl) and where halogen is selected from chlorine, bromine and fluorine.

The present invention also includes novel compositions of matter containing the above-defined compounds which are useful as neurotropic agents, anxiolytic agents and/or antihypertensive agents in mammals and the methods for treating cognitive and related neural behavioral problems, anxiety and/or hypertension in mammals therewith. The present invention also includes a process for the chemical synthesis of the novel compounds disclosed herein.

DETAILED DESCRIPTION OF THE INVENTION

The novel compounds of the present invention are obtainable as colorless to yellow crystalline materials having characteristic melting points and absorption spectra. They are generally soluble in organic solvents such as lower alkanols, chloroform, tetrahydrofuran, N,N-dimethylformamide, dichloromethane, acetone and the like but are generally insoluble in water.

The novel N-((dialkylamino)methylene)substituted-pyrazolo(1,5-a)pyrimidine-3-carboxamide and N-((dialkylamino)methylene)substituted-4,5-dihydropyrazolo(1,5-a)-pyrimidine-3-carboxamide compounds of the present invention may be readily prepared as set forth in the following general reaction schemes:

(a) reacting a compound of the formula:

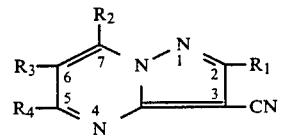

wherein $R_1$, $R_2$, $R_3$ and $R_4$ are as defined above with an acid to produce a compound of the formula

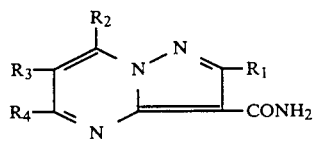

wherein $R_1$, $R_2$, $R_3$ and $R_4$ are as defined above; and either (b) reacting the product of step (a) with a compound of the formula

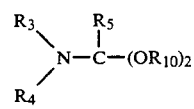

wherein $R_5$, $R_8$ and $R_9$ are as defined above and $R_{10}$ is a $C_1$ to $C_3$ alkyl group or a $C_1$ to $C_6$ cycloalkyl group to produce a compound of the formula

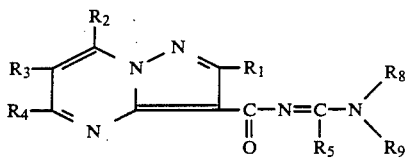

wherein $R_1$, $R_2$, $R_3$, $R_4$, $R_5$, $R_8$, $R_9$ and $R_{10}$ are as defined above; or (c) (i) reacting the product of step (a) with selective reducing agent reagent to produce a compound of the formula

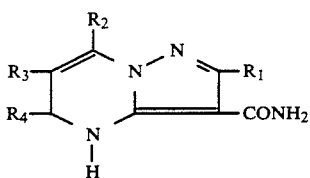

wherein $R_1$, $R_2$, $R_3$ and $R_4$ are as defined above; and (c) (ii) reacting the product of step (c) (i) with a compound of the formula

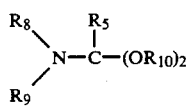

wherein $R_5$, $R_8$, $R_9$ and $R_{10}$ are as defined above to produce a compound of the formula

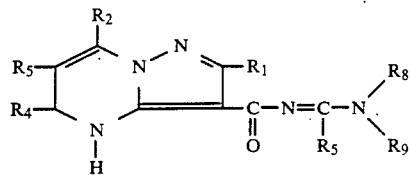

wherein $R_1$, $R_2$, $R_3$, $R_4$, $R_5$, $R_8$ and $R_9$ are as defined above.

In a preferred embodiment the compounds of the present invention may be prepared by the following preferred reaction scheme.

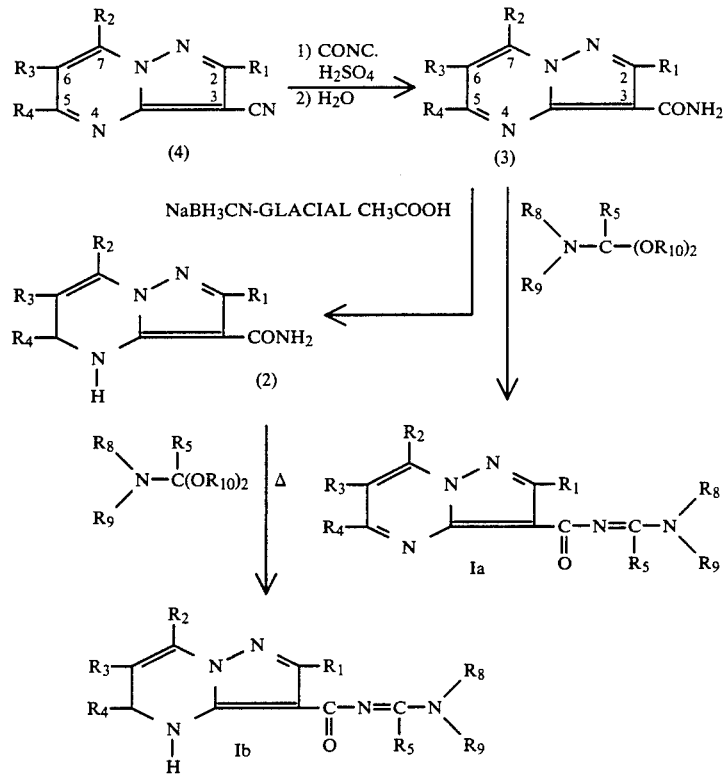

wherein $R_1$, $R_2$, $R_3$, $R_4$, $R_5$, $R_8$ and $R_9$ are as above defined and $R_{10}$ is $C_1$ to $C_3$ alkyl or $C_1$ to $C_6$ cycloalkyl.

As shown hereinabove a pyrazolo(1,5-a)pyrimidine-3-carbonitrile (4) (prepared in the manner described in U.S. Pat. Nos. 4,281,000; 4,236,005 and 4,178,499) is stirred with concentrated sulfuric acid at room temperature for from 2-20 hours. The mixture is carefully poured onto ice and the precipitate is collected, neutralized with sodium hydroxide, ammonium hydroxide or saturated sodium bicarbonate and the like and washed with water to obtain the corresponding pyrazolo(1,5-a)pyrimidine-3-carboxamide compound (3).

The carboxamide compound (3) is heated at the reflux temperature with an N,N-dialkyl carboxamide dialkyl acetal, such as N,N-dimethylformamide dimethyl acetal, N,N-dimethylformamide diethyl acetal or N,N-dimethylformamide dicyclohexyl acetal for 1-30 hours, and then is cooled. The solvent is evaporated in vacuo and the residue is purified by conventional means to obtain the N-((dialkylamino)methylene)-substituted pyrazolo (1,5-a)pyrimidine-3-carboxamide compounds Va, where $R_5$ is hydrogen. When N,N-dimethylacetamide dimethyl acetal is substituted for N,N-dimethylformamide dimethyl acetal in the above procedure the compounds Va where $R_5$ is methyl are obtained.

Alternatively when the carboxamide (3) is reacted with sodium cyanoborohydride or an equivalent selective reducing agent like lithium aluminum hydride, or the like, by stirring in glacial acetic acid under nitrogen in an ice bath for approximately one hour, then at room temperature for from 1–12 hours, the resulting precipitate is collected and washed with water. The solid is dissolved in an inert solvent such as dichloromethane or acetonitrile and the like and washed with saturated sodium bicarbonate solution.

Separation and evaporation of the organic phase gives the crude N-((dialkylamino)methylene) substituted-4,5-dihydropyrazolo(1,5-a)pyrimidine-3-carboxamide product (2) which is recrystallized from a solvent such as isopropyl alcohol or acetonitrile and the like or from a mixture of solvents such as ether-hexane, chloroform-methanol or N,N-dimethylformamideacetonitrile and the like. The 4,5-dihydro-3-carboxamide (2) is then heated at the reflux temperature with N,N-dimethylformamide dimethyl acetal, N,N-dimethylacetamide dimethyl acetal according to the procedure hereinabove described, to obtain the N-((dialkylamino)methylene)-substituted-4,5-dihydropyrazolo (1,5-a)pyrimidine-3-carboxamide compounds Vb where $R_5$ is hydrogen or the N-((dialkylamino)methylene) substituted-4,5-dihydropyrazolo(1,5-a)pyrimidine-3-carboxamide compounds Vb where $R_5$ is methyl, respectively.

The novel compounds of the present invention possess the ability to enhance neural function in warm-blooded animals affected by behavioral neurological problems including the cognitive deterioration associated with decreased neural function which occurs with cerebral insufficiency, aging, dementia, and similar conditions.

A useful in vivo test that measures how effectively central nervous system-acting drugs enhance survival in an hypoxic environment, presumably by improving the ratio of energy supply to demand is known as the Hypoxic Survival Test. This test demonstrates the ability of the test compounds relative to known parasympathomimetic agent physostigmine. This test shows the enhanced survival of test animals in an hypoxic environment after treatment with drug as compared to saline treated control animals without drug. Extensive testing has demonstrated that under conditions of 10 percent oxygen, only 5–20 percent of control mice (treated with saline) survive after 5 minutes, whereas 60–80 percent of the physostigmine treated mice survice. Drugs are tested by intraperitoneally injecting groups of mice 30 minutes prior to placing them in hypoxic mixture and measuring survival. The rationale of this test is that drugs which enhance survival under hypoxic conditions without concomitant, depression or sedative side effects, may do so by enhancing energy metabolism, or by preserving normal brain function under conditions of reduced energy metabolism. Given the dependence of the brain on a constant supply of energy, drugs which have this property may have many far-reaching therapeutic indications, including recovery from stroke and closed head injury, as well as reducing the deleterious effects of the aging central nervous system. For example, in aged and senile demented patients, energy metabolism is known to be deficient, and is thought to contribute significantly to the neurochemical and neurophysiological dysfunctions of aging.

Groups of 20 Royal Hart mice (6 weeks of age) are injected intraperitoneally with test compound (0.1–100 mg/kg) 30 minutes prior to placing them in a hypoxic mixture (10 percent oxygen in 90 percent carbon dioxide) and measuring survival after 5 minutes.

A separate group of 20 mice is injected intraperitoneally with saline solution (0.01 cc/g of body weight) and processed as described above.

Still another group of 20 mice is injected intraperitoneally with 0.125 mg/kg of physostigmine and processed as described above.

Results of this test on representative compounds of the present invention are Table I.

TABLE I

| Compound | Hypoxic Survival Test Dose mg/kg | % Survivors |
|---|---|---|
| N-((Dimethylamino)methylene)-2-methyl-7-(4-pyridinyl)pyrazolo-(1,5-a)pyrimidine-3-carboxamide | 10 | 55 |
| N-((Dimethylamino)methylene)-7-(3-pyridinyl)pyrazolo(1,5-a)pyrimidine-3-carboxamide | 25 | 80 |
|  | 25 | 58 |
|  | 25 | 42 |
| N-((Dimethylamino)methylene)-2-methyl-7-phenylpyrazolo(1,5-a)-pyrimidine-3-carboxamide | 0.1 | 45 |
|  | 10 | 100 |
|  | 100 | 97 |
|  | 200 | 95 |
| N-((Dimethylamino)methylene)-2,5-dimethyl-7-phenylpyrazolo(1,5-a)-pyrimidine-3-carboxamide | 100 | 42 |
| N-((Dimethylamino)methylene)-6-methyl-pyrazolo(1,5-a)pyrimidine-3-carboxamide | 10 | 42 |
|  | 50 | 40 |
|  | 100 | 62 |
|  | 200 | 45 |
| N-((Dimethylamino)methylene)-4,5-dihydro-7-(3-(trifluoromethyl)phenyl)pyrazolo-(1,5-a)pyrimidine-3-carboxamide | 50 | 75 |
|  | 100 | 57 |

Another in vivo test associated with decreased neural function in mammals is the Passive-Avoidance Anoxic-Induced-Amnesia Test. This test is used to determine the attenuation of anoxic induced amnesia in mice treated with drug, as compared to saline treated control animals with no drug.

A shock-motivated, single trial, step-through passive avoidance procedure is used. Groups of 25 Swiss-Webster, middle aged mice (9 months of age) are placed singly in the front chamber of a 2-chamber box and are allowed to voluntarily cross into the rear chamber. As soon as the mouse enters the rear chamber, a door automatically traps the animal and a mild electric shock (0.4 mA for 4 seconds) is delivered to its feet. Following the foot shock, the mice are initially placed in an anoxic environment (0 percent oxygen) for 12 seconds, which quickly induces unconsciousness. They are then placed in a hypoxic environment (15 percent oxygen) for four minutes which prolongs the oxygen deprived state, maintaining unconsciousness. All testing is performed 24 hours later, and in all cases the mice appear fully recovered from the previous anoxic/hypoxic treatment. All test compounds are administered intraperitoneally at a dose of 5–200 mg/kg, 30 minutes prior to training and testing. Control animals are injected intraperitoneally only with saline at 0.01 cc/g of body weight.

The latency to enter the rear chamber is recorded for both training and testing. Presumably, the more the animal remembers being shocked, the greater it will inhibit going into the rear chamber and the higher will be its latency to re-enter. An improvement of 30 percent over saline control scores is considered active. The results of this test on representative compounds of the present invention appear in Table II.

TABLE II

Passive-Avoidance Anoxic-Induced-Amnesia Test

| Compound | Dose mg/kg | % Improvement |
|---|---|---|
| N-((Dimethylamino)methylene)-7-(3-pyridinyl)pyrazolo(1,5-a)-pyrimidine-3-carboxamide | 25<br>50 | 33<br>33 |
| N-((Dimethylamino)methylene)-2-methyl-7-phenylpyrazolo(1,5-a)pyrimidine-3-carboxamide | 5<br>10<br>25<br>50 | 49<br>37<br>66<br>66 |
| N-(1-(Dimethylamino)ethylidene)-7-(3-pyridinyl)pyrazolo(1,5-a)-pyrimidine-3-carboxamide | 25<br>50 | 53<br>46 |
| N-((Dimethylamino)methylene)-4,5-dihydro-7-(3-(trifluoromethyl)phenyl)-pyrazolo(1,5-a)pyrimidine-3-carboxamide | 25<br>50 | 49<br>57 |
| N-((Dimethylamino)methylene)-4,5-dihydro-7-(3-pyridinyl)pyrazolo-(1,5-a)pyrimidine-3-carboxamide | 50<br>100 | 66<br>54 |

Certain of the novel compounds of the present invention possess central nervous system activity at non-toxic doses and as such are useful as anxiolytic agents. They produce certain responses in standard tests with laboratory animals which are known to correlate well with relief of anxiety in human beings. The compounds, when tested pharmacologically, are found to have a desirable wide spread between doses producing anxiolytic activity and toxic symptoms.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2 percent starch vehicle containing 0.5 percent v/v polyethylene glycol and one drop of Polysorbate 80, or distilled water and one drop of Polysorbate 80 to groups of at least four rats. At 30 or 60 minutes, the rats were treated intravenously with pentylenetetrazole at a dose of 23 mg/kg of body weight. This dose is estimated to cause clonic seizures in 99 percent of unprotected rats. The test compounds are considered active if they protect 50 percent or more of the rats from clonic seizures.

It has been reported (R. T. Hill and D. H. Tedeschi, "Animal Testing and Screening Procedures in Evaluating Psychotropic Drugs" in "An Introduction to Psychopharmacology", pp 237–288 (Eds. R. R. Rech and K. E. Moore, Raven Press, New York, 1971)) that there is a high degree of correlation between antagonism of pentylenetetrazole seizures in rats and anti-anxiety effects in higher warm-blooded animals.

The results of this test on representative compounds of the present invention appear in Table III.

TABLE III

Protection Against Clonic Seizures Caused by Pentylenetetrazole in Rats

| Compound | Dose mg/kg | % of Rats Protected |
|---|---|---|
| N-((Dimethylamino)methylene)-7-(3-methylphenyl)pyrazolo(1,5-a)pyrimidine-3-carboxamide | 50 | 50 |
| N-((Dimethylamino)methylene)-4,5-dihydro-7-(3-(trifluoromethyl)phenyl)pyrazolo-(1,5-a)pyrimidine-3-carboxamide | 25<br>25<br>12.5 | 75<br>88<br>88 |

TABLE III-continued

Protection Against Clonic Seizures Caused by Pentylenetetrazole in Rats

| Compound | Dose mg/kg | % of Rats Protected |
|---|---|---|

Another test used to assess anti-anxiety effects is a non-conditioned passive avoidance procedure described by J. R. Vogel, G. Beer and D. E. Clody, "A Simple and Reliable Conflict Procedure for Testing Antianxiety Agents", Psychopharmacologia, 21, 1–7 (1971). A conflict situation was induced in rats by a modification of this method.

Groups of 8 naive, Wistar strain rats, weighing 200–240 g each, were deprived of water for 48 hours. The test compounds were administered in single or graded, oral doses, suspended in 2 percent starch with 5 percent polyethylene glycol in distilled water and one drop of Polysorbate 80. Control animals received the vehicle alone. At 60 minutes each rat was placed in an individual clear plastic chamber. Tap water was available ad libitum from a nipple located in a black box off the main chamber. A 0.7 milliampere AC shocking current was established between the stainless steel grid floor and the tap. After 20 licks of non-shocked drinking, a 2 second shocking current was administered to the rat. This ratio of 20 licks of non-shocked drinking followed by a 2 second shock was continued for a total of 3 minutes. The number of shocks taken by each rat during the 3 minute interval was recorded and compared to a control group.

The test compounds are considered active if the number of shocks received by the test group is significantly higher than the control group by the Mann-Whitney U test. That is, the test compounds are considered active if they result in the treated rat taking slightly more than double the number of shocks that the untreated rat will take. Results of this in vivo test on a representative compound of the present invention given in Table IV.

TABLE IV

Conflict Procedure In Rats

| Compound | Dose mg/kg | Result (no. of shocks per 3 min.) |
|---|---|---|
| N-((Dimethylamino)methylene-4,5-dihydro-7-(3-trifluoromethyl)-phenyl)pyrazolo(1,5-a)pyrimidine-3-carboxamide | 25 | 22.9 |

Still another test utilized for the determination of anxiolytic activity is the measurement of the ability of a test compound to inhibit the binding of tritiated benzodiazepines to brain-specific receptors of mammals. A modification of the method described by R. F. Squires, et al, Nature, 266, No. 21: 732 (April, 1977) and H. Mosler, et al, Science, 198: 849 (1977) was employed.

Male albino rats (Wistar strain, weighing 150–200 g each) were used. The test compounds were solubilized in N,N-dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl(pH 7.4), or (2) resuspended in one-half of the original volume in hypotonic 10 mM Tris.HCL (pH 7.4) and frozen (−20° C.) until time of use. Frozen P₂ preparations were thawed and resuspended in four times the original homogenizing volume at time of assay.

The binding assay consisted of 300 l of the P₂-fraction suspension (0.2–0.4 mg protein), 100 l of test drug and 100 l of ³H-diazepam 91.5 nM, final concentration) or ³H-flunitrazepam (1.0 nM, final concentration) which was added to 1.5 l of 50 mM Tris.HCl (pH 7.4). Non-specific binding controls and total binding controls received 100 ml of diazepam (3M final concentration) and 100 l of deionized water, respectively, in place of the test compound. Incubation for 30 minutes proceeded in ice and was terminated by filtration, under vacuum, through glass fiber filters. The filters were washed twice with 5 ml of ice-cold 50 mM Tris.HCl (pH 7.4) and placed in scintillation vials. After drying at 50°–60° C. for 30 minutes, 10 ml of diluent was added and the radioactivity determined in a scintillation counter.

Inhibition of binding was calculated by the difference between total binding and binding in the presence of test compound, divided by the total, times 100. Physiological activity can be shown by a test compound that inhibits ³H-benzodiazepine binding by 12 percent or more. Such in vitro activity is biologically relevant when the test compound also demonstrates statistically significant anxiolytic activity through in vivo studies.

The result of this in vitro test on representative compounds of this invention are given in Table V.

TABLE V

| Inhibition of the Binding of ³H-Benzodiazepine to Brain-Specific Receptors of Rats | |
|---|---|
| Compound | % Inhibition |
| N-((Dimethylamino)methylene)-7-phenyl-pyrazolo(1,5-a)pyrimidine-3-carboxamide | 28 |
| N-((Dimethylamino)methylene)-7-(3-methyl-phenyl)pyrazolo(1,5-a)pyrimidine-3-carboxamide | 65 |
| N-(Dimethylamino)methylene)-7-(3-trifluoromethyl)phenyl)pyrazolo(1,5-a)-pyrimidine-3-carboxamide | 82 |
| N-((Dimethylamino)methylene)-2-methyl-7-phenylpyrazolo(1,5-a)pyrimidine-3-carboxamide | 18 |
| N-((Dimethylamino)methylene)-4,5-dihydro-7-(3-trifluoromethyl)phenyl)pyrazolo-(1,5-a)pyrimidine-3-carboxamide | 17 |
| N-((Dimethylamino)methylene)-4,5-dihydro-7-(3-pyridinyl)pyrazolo(1,5-a)pyrimidine-3-carboxamide | 32 |

Certain of the novel compounds of the present invention are active hypotensive agents at non-toxic doses when administered to mammals. These compounds were tested for hypotensive activity by the method of P. S. Chan and D. W. Poorvin, Clinical and Experimental Hypertension, 1 (6), 817-813 (1979). Male, 16 week old spontaneously hypertensive rats of the Okamoto strain having an average mean arterial blood pressure of 160±1.5 mm of mercury are used in the test. One to three rats are used per test compound. A rat is dosed by gavage with a test compound, suspended in 2 percent pre-boiled starch at a concentration of 50 mg/ml, at a dose of 100 mg/kg of body weight or less, with 0.9 percent sodium chloride loading at a dose of 25 ml/kg of body weight. A second identical dose of the test compound, without sodium chloride loading is given 24 hours later. At 28 hours after the initial dose the mean arterial blood pressure is measured by the method of Chan and Poorvin vide supra. The procedure is repeated in a second and third rat when necessary.

The results of this test on representative compounds of the present invention appear below in Table VI.

TABLE VI

| Reduction of Mean Arterial Blood Pressure in Spontaneously Hypertensive Rats | |
|---|---|
| Compound | MABP/mmHg (no. of rat) |
| N-((Dimethylamino)methylene)-2-methyl-7-(4-pyridinyl)pyrazolo(1,5-a)pyrimidine-3-carboxamide | 130(2) |
| N-((Dimethylamino)methylene)-4,5-dihydro-7-(3-(trifluoromethyl)phenyl)pyrazolo-(1,5-a)pyrimidine-3-carboxamide | 131(3) |
| N-((Dimethylamino)methylene)-4,5-dihydro-7-(3-pyridinyl)pyrazolo(1,5-a)pyrimidine-3-carboxamide | 113(1) |

The novel compounds of the present invention have been found to be useful as agents for the treatment of cognitive and related neural behavioral problems in mammals when administered in amounts ranging from 5 mg to about 200 mg/kg of body weight per day. A preferred dosage regimen for optimum results would be from about 10 mg to about 50 mg/kg of body weight per day and such dosage units are employed so that a total of from about 700 mg to about 3.5 g of the active compound for a subject of about 70 kg of body weight are administered in a 14 hour period.

Certain of the novel compounds of the present invention have been found to be useful for meliorating anxiety in mammals when administered in amounts ranging from about 0.5 mg to about 100 mg/kg of body weight per day. A preferred dosage regimen for optimum results would be from about 1.0 mg to about 50 mg/kg of body weight per day, and such dosage units are employed so that a total of from about 700 mg to about 3.5 g of the active compound for a subject of about 70 kg of body weight are administered in a 24 hour period.

Certain of the novel compounds of the present invention have been found to be highly useful for lowering elevated blood pressure in mammals when administered in amounts ranging from 2.0 mg to about 100 mg/kg of body weight per day. A preferred dosage regimen for optimum results would be from about 50 mg to about 750 mg per dose. Such dosage units are employed so that a total of from about 200 mg to about 3.0 g of the active compound for a subject of about 70 kg of body weight are administered in a 24 hour period.

The hereinabove described dosage regimen for treating neural behavioral problems, meliorating anxiety and lowering elevated blood pressure in mammals may be adjusted to provide the optimum therapeutic response. For example, several divided doses may be administered daily or the dose may be proportionally reduced as indicated by the exigencies of the therapeutic situation. A decided practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1 percent of active compound. The percentage of the compositions and preparations may, of course, be varied and may conveniently be between from about 2 percent to about 60 percent of the weight of the unit. The amount of active compound in such therapeutically useful compositions is such that a suitable dosage will be obtained. Preferred compositions or preparations according to the present invention are prepared so that an oral dosage unit form contains between about 5 and 200 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such a peppermint, oil of wintergreen or cherry flavoring agent. When the dosage unit form is a capsule it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained release preparations and formulations.

These active compounds may be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

DESCRIPTION OF PREFERRED EMBODIMENTS

The invention will be described in greater detail in conjunction with the following specific examples. They are not to be construed to limit the claims in any manner whatsoever.

EXAMPLE 1

7-(3-Methylphenyl)pyrazolo(1,5-a) pyrimidine-3-carbonitrile

A mixture of 50.0 g of 3-methylacetophenone and 60 ml of N,N-dimethylformamide dimethylacetal is heated at reflux for 16 hours. The reaction mixture is then evaporated in vacuo to give an oil. The oil is treated with dichloromethane/hexane to crystallize 54.50 g of 3-dimethylamino-3'-methylacrylophenone.

A stirred mixture of 10.82 g of 5-amino-4-pyrazolecarbonitrile and 18.92 g of the preceding product in 50 ml of glacial acetic acid is heated at reflux for 7 hours. The reaction mixture is cooled, evaporated, and the residue dissolved in dichloromethane and washed with a saturated sodium bicarbonate solution. The organic layer is dried over anhydrous sodium sulfate and passed through a short column of hydrous magnesium silicate, and then hexane is added to the eluate until crystallization occurs. The solid is collected by filtration and recrystallized from dichloromethane-hexane to give 10.60 g of the desired product, mp 161°–162° C.

EXAMPLE 2

2-Methyl-7-(4-pyridinyl)pyrazolo(1,5-a) pyrimidine-3-carbonitrile

A mixture of 6.1 g of 5-amino-3-methyl-4-pyrazole carbonitrile and 8.81 g of 3-dimethylamino-1-(4-pyridinyl)-2-propen-1-one in 50 ml of glacial acetic acid is stirred and heated at reflux for 5 hours. The reaction mixture is cooled and the precipitate which forms is collected by filtration and washed with water and a little dichloromethane to give a solid. The solid is partitioned between saturated sodium bicarbonate and dichloromethane. The organic layer is dried over anhydrous sodium sulfate and passed through a short column of hydrous magensium silicate. The addition of hexane to the eluate crystallizes the product which is collected by filtration to give 6.17 g of the desired product, mp 220°–221° C.

EXAMPLE 3

2,5-Dimethyl-7-phenylpyrazolo(1,5-a) pyrimidine-3-carbonitrile

To a solution of 17.4 g of benzoylacetone in 100 ml of ethyl acetate is added a solution of 7.35 g of pyrrolidine in 50 ml of ethyl acetate. The reaction mixture is stirred at room temperature for 16 hours. The precipitated compound is collected by filtration to give 20.30 g of 3-(1-pyrrolidinyl)crotonophenone.

A mixture of 4.88 g of 5-amino-3-methyl-4-pyrazolecarbonitrile and 8.61 g of 3-(1-pyrrolidinyl)-crotonophenone in 50 ml of glacial acetic acid is stirred and heated at reflux for 6 hours. The reaction mixture is cooled and the procedure described in Example 2 is then followed to obtain 7.77 g of the desired product, mp 175°–177° C.

EXAMPLE 4

6-Methylpyrazolo(1,5-a)pyrimidine-3-carbonitrile

By the procedure described in Example 2, 5.40 g of 5-amino-4-pyrazolecarbonitrile is reacted with 5.70 g of 3-ethoxy-2-methylacrolein in 25 ml of glacial acetic acid to give the desired product as colorless prisms, mp 193°–194° C.

EXAMPLE 5

7-(3-Trifluoromethyl)phenylpyrazolo(1,5-a) pyrimidine-3-carboxamide

A mixture of 3.0 g of 7-(α,α,α-trifluoro-m-tolyl)-pyrazolo(1,5-a)pyrimidine-3-carbonitrile (prepared as described in U.S. Pat. No. 4,236,005) and 150 ml of concentrated sulfuric acid is stirred at room temperature for 4 hours. The solution is then carefully poured into ice water with stirring. The white precipitate which forms is collected, washed with water and then with saturated sodium bicarbonate until it is neutral. The solid is heated with one liter of isopropyl alcohol and filtered. The white solid is then dried in vacuo to give the desired product as a colorless solid, mp 256°–258° C.

EXAMPLE 6

7-(2,5-Dichlorophenyl)-2-methylpyrazolo(1,5-a-) pyrimidine-3-carboxamide

A mixture of 31.0 g of 2',5'-dichloroacetophenone and 25 ml of N,N-dimethylformamide dimethyl acetal is heated on a steam bath for 6 hours, then evaporated to dryness in vacuo. The residue is slurried with hexane, and filtered to give 35.3 g of 2',5'-dichloro-3-dimethylaminoacrylophenone as orange crystals, mp 83°–85° C.

A mixture of 12.2 g of 3-amino-4-cyano-5-methylpyrazole and 24.4 g of 2',5'-dichloro-3-dimethylaminoacrylophenone in 250 ml of glacial acetic acid is heated on a steam bath for 4 hours. The mixture is cooled and filtered to give 21.28 g of 7-(2,5-dichlorophenyl)-2-methylpyrazolo(1,5-a)pyrimidine-3-carbonitrile as off-white crystals.

21.28 g of the preceding product is dissolved in concentrated sulfuric acid and stirred for 5 hours. The solution is carefully poured onto ice. The precipitate which forms is collected by filtration, washed with water and air dried to give the desired product as colorless crystals, mp 234°–236° C.

EXAMPLES 7-16

Additional pyrazolo(1,5-a)pyrimidine-3-carboxamides which are prepared from the corresponding pyrazolo(1,5-a)pyrimidine-3-carbonitriles in the manner described in Examples 5 are listed in Table VII.

The pyrazolo(1,5-a)pyrimidine-3-carbonitriles are prepared by the procedures described in U.S. Pat. Nos. 4,178,449; 4,236,005; and 4,281,000 by reacting the approximate 3-(dimethylamino)acrylophenone intermediate with an appropriately substituted 3-aminopyrazole-4-carbonitrile.

TABLE VII

Pyrazolo(1,5-a)pyrimidine-3-carboxamides

| Example | Compound | $R_1$ | $R_2$ | $R_3$ | $R_4$ | MP °C. |
|---|---|---|---|---|---|---|
| 7 | 7-Phenylpyrazolo(1,5-a)pyrimidine-3-carboxamide | H | phenyl | H | H | 236–238.5 |
| 8 | 2-Methyl-7-phenylpyrazolo(1,5-a)pyrimidine-3-carboxamide | $CH_3$ | phenyl | H | H | 233–235 |
| 9 | 7-(3-Pridinyl)pyrazolo(1,5-a)pyrimidine 3-carboxamide | H | 3-pyridinyl | H | H | 285–236 |
| 10 | 7-(4-Pyridinyl)pyrazolo(1,5-a)pyrimidine-3-carboxamide | H | 4-pyridinyl | H | H | 394–396 |
| 11 | 7-(3-Fluorophenyl)pyrazolo(1,5-a) pyrimidine-3-carboxamide | H | 3-fluorophenyl | H | H | 247–249 |

TABLE VII-continued

Pyrazolo(1,5-a)pyrimidine-3-carboxamides

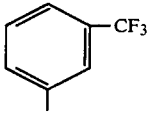

| Example | Compound | $R_1$ | $R_2$ | $R_3$ | $R_4$ | MP °C. |
|---------|----------|-------|-------|-------|-------|--------|
| 12 | 2-Methyl-7-((3-trifluoromethyl)phenyl)pyrazolo(1,5-a)pyrimidine-3-carboxamide | $CH_3$ | 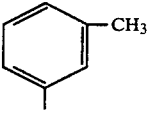 | H | H | 209.5–210.5 |
| 13 | 7-(3-Methylphenyl)pyrazolo(1,5-a)pyrimidine-3-carboxamide | H | 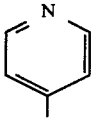 | H | H | 228–229 |
| 14 | 2-Methyl-7-(4-pyridinyl)pyrazolo(1,5-a)-pyrimidine-3-carboxamide | $CH_3$ | 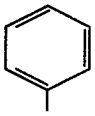 | H | H | 286–288 |
| 15 | 2,5-Dimethyl-7-phenylpyrazolo(1,5-a)-pyrimidine-3-carboxamide | $CH_3$ |  | H | $CH_3$ | 212–213 |
| 16 | 6-Methylpyrazolo(1,5-a)pyrimidine-3-carboxamide | H | H | $CH_3$ | H | 251–253 |

EXAMPLE 17

4,5-Dihydro-7-(3-(trifluoromethyl)phenyl)pyrazolo-(1,5-a)pyrimidine-3-carboxamide A 10.0 g amount of 7-(3-trifluoromethyl)phenyl)-pyrazolo(1,5-a)pyrimidine-3-carboxamide (prepared as described in Example 5) is stirred under nitrogen as a suspension in 120 ml of glacial acetic acid (cooled in an ice bath) and then 5.5 g of sodium cyanoborohydride is added to the reaction mixture in portions, with an additional 80 ml of glacial acetic acid. After one hour of stirring in the ice bath the mixture is stirred at room temperature for 19 hours. The solution is evaporated to dryness, then water is added and the white precipitate which forms is collected by filtration and washed with an aqueous saturated solution of sodium bicarbonate, then with water. The solid is treated with 100 ml of acetonitrile, then collected and dried to give 5.25 g of the desired product which is recrystallized from acetonitrile, mp 157°–160° C.

EXAMPLE 18

4,5-Dihydro-7-(3-pyridinyl)pyrazolo(1,5-a)pyrimidine-3-carboxamide

A 20.0 g amount of 7-(3-pyridinyl)pyrazolo (1,5-a)-pyrimidine-3-carboxamide (prepared as described in Example 9) is suspended in 200 ml of glacial acetic acid under nitrogen with stirring at room temperature. Then 14.0 g of sodium cyanoborohydride is added in portions and the mixture is stirred for 3 hours. The mixture is then allowed to stand at room temperature for 16 hours, and then the reaction mixture evaporated to dryness. Water is added to the residue followed by saturated sodium bicarbonate until a pH of about 8.0 is achieved and a gummy solid precipitated. The solid is collected by filtration and then dissolved in acentonitrile. Evaporation of the organic solvent gives 10.0 g of a yellow solid (A). The aqueous filtrate above is evaporated to dryness in vacuo and this residue is extracted with acetonitrile. Evaporation of the solvent gives a yellow gummy solid (B). The solids (A) and (B) are combined and triturated with isopropyl alcohol to give a yellow solid precipitate which is isolated and dried in vacuo to give 61.9 g of the desired product which is then recrystallized from isopropyl alcohol-acetonitrile, mp 182°–184° C.

EXAMPLE 19

7-(3-Fluorophenyl)-4,5-dihydropyrazolo(1,5-a) pyrimidine-3-carboxamide

To a stirred mixture of 136.3 g of 7-(3-fluorophenyl)-pyrazolo(1,5-a)pyrimidine-3-carboxamide (prepared as described in Example 11) in one liter of glacial acetic acid at room temperature under nitrogen is added 83.6 g of sodium cyanoborohydride in portions. The mixture is stirred at room temperature for 16 hours. The crystals that form are collected by filtration and triturated with saturated sodium bicarbonate until a pH of 7–8 is achieved. The crystals are then filtered, washed with excess water and dried in vacuo to give 63.0 g of the desired product of the example as cream colored crystals, mp 122°–125° C.

EXAMPLE 20

N-((Dimethylamino)methylene)-7-phenylpyrazolo(1,5-a)pyrimidine-3-carboxamide

A mixture of 600 mg of 7-phenylpyrazolo(1,5-a)pyrimidine-3-carboxamide (Example 7), 5.0 ml of N,N-dimethylformamide dimethyl acetal and 25.0 ml of dichloromethane are heated on a steam bath for 2 hours with complete solution taking place. The solution is evaporated in vacuo to give a solid. The solid is then recrystallized from acetone to give 58 mg of the desired product as yellow needles, mp 198°–201.5° C.

EXAMPLE 21

N-((Dimethylamino)methylene)-2-methyl-7-((3-trifluoromethyl)phenyl)pyrazolo(1,5-a)pyrimidine-3-carboxamide A mixture of 1.67 g of 2-methyl-7-(3-trifluoromethyl)phenyl)pyrazolo(1,5-a)pyrimidine-3-carboxamide (Example 12) and 5.0 ml of N,N-dimethylformamide dimethyl acetal is heated on a steam bath for one hour to give a solution. The solution is cooled and the precipitate that forms is collected by filtration to give 1.82 g of the desired product as pale yellow prisms, mp 174°–175.5° C.

EXAMPLE 22

N-((Dimethylamino)methylene)-7-(3-methylphenyl)-pyrazolo(1,5-a)pyrimidine-3-carboxamide A mixture of 6.0 g of 7-(3-methylphenyl) pyrazolo(1,5-a)pyrimidine-3-carboxamide (Example 13) and 15 ml of N,N-dimethylformamide dimethyl acetal is heated on a steam bath for 4 hours to give a solution. The solution is evaporated in vacuo to give a solid. The solid is recrystallized twice from dichloromethane-hexane to give 4.70 g of the desired product as colorless crystals, mp 165°–166° C.

EXAMPLES 23–31

Additional N-((dimethylamino)methylene) pyrazolo(1,5-a)pyrimidine-3-carboxamide and N-((dimethylamino)methylene)-4,5-dihydropyrazolo(1,5-a)pyrimidine-3-carboxamide products are prepared from the corresponding pyrazolo(1,5-a)pyrimidine-3-carboxamide or the 4,5-dihydropyrazolo(1,5-a)pyrimidine-3-carboxamide intermediate compounds by heating with N,N-dimethylformamide dimethyl acetal in the manner described in Examples 20–22 and are listed in Table VIII.

TABLE VIII

N-((Dimethylamino)methylene)pyrazolo(1,5-a)pyrimidine-3-carboxamides and N-((Dimethylamino)methylene)4,5-dihydropyrazolo(1,5-a)pyrimidine-3-carboxamides

| Example | Precursor | Compound | MP°C. |
|---|---|---|---|
| 23 | Example 5 | N-((Dimethylamino)methylene)-7-(3-trifluoromethyl)phenyl)pyrazolo(1,5-a)pyrimidine-3-carboxamide | 156–158 |
| 24 | Example 14 | N-((Dimethylamino)methylene)-2-methyl-7-(4-pyridinyl)pyrazolo(1,5-a)pyrimidine-3-carboxamide | 198–200 |
| 25 | Example 9 | N-((Dimethylamino)methylene)-7-(3-pyridinyl)-pyrazolo(1,5-a)pyrimidine-3-carboxamide | 209–211 |
| 26 | Example 8 | N-((Dimethylamino)methylene)-2-methyl-7-phenylpyrazolo(1,5-a)pyrimidine-3-carboxamide | 150–152 |
| 27 | Example 15 | N-((Dimethylamino)methylene)-2,5-dimethyl-7-phenylpyrazolo(1,5-a)pyrimidine-3-carboxamide | 210–212 (dec.) |
| 28 | Example 16 | N-((Dimethylamino)methylene)-6-methyl-pyrazolo(1,5-a)pyrimidine-3-carboxamide | 213–215 |
| 29 | Example 6 | 7-(2,5-Dichlorophenyl)-N-((dimethylamino)-methylene-2-methylpyrazolo(1,5-a)pyrimidine-3-carboxamide | 195–197 |
| 30 | Example 17 | N-((Dimethylamino)methylene)-4,5-dihydro-7-(3-(trifluoromethyl)phenylpyrazolo(1,5-a)-pyrimidine-3-carboxamide | 133–135 |
| 31 | Example 18 | N-((Dimethylamino)methylene)4,5-dihydro-7-(3-pyridinyl)pyrazolo(1,5-a)pyrimidine-3-carboxamide | 132–135 |

EXAMPLES 32–34

Other N-((dimethylamino)methylene)pyrazolo (1,5-a)-pyrimidine-3-carboxamide and N-((dimethylamino)methylene)-4,5-dihydropyrazolo(1,5-a)pyrimidine-3-carboxamide products which are prepared from corresponding pyrazolo(1,5-a)pyrimidine-3-carboxamide or the 4,5-dihydropyrazolo(1,5-a)pyrimidine-3-carboxamide intermediate compounds by heating with N,N-dimethylformamide dimethyl acetal in the manner described in Examples 20–22 are listed in Table IX.

TABLE IX

N-((Dimethylamino)methylene)pyrazolo(1,5-a) pyrimidine-3-carboxamides and N-((Dimethylamino) methylene)-4,5-dihydropyrazolo(1,5-a)pyrimidine-3-carboxamides

| Example | Presursor | Compound |
|---|---|---|
| 32 | Example 10 | N-((Dimethylamino)methylene)-7-(4-pyridinyl)pyrazolo(1,5-a) pyrimidine-3-carboxamide |
| 33 | Example 11 | 7-(3-Fluorophenyl)-N-((dimethylamino)methylene)pyrazolo(1,5-a)-pyrimidine-3-carboxamide |
| 34 | Example 19 | 7-(3-Fluorophenyl)-N-((dimethylamino)methylene)-4,5-dihydro-pyrazolo(1,5-a)pyrimidine-3-carboxamide |

EXAMPLE 35

N-((Dimethylamino)ethylidene)-7-(3-pyridinyl)-pyrazolo(1,5-a)pyrimidine-3-carboxamide A mixture of 10.0 g of 7-(3-pyridinyl)pyrazolo(1,5-a)pyrimidine-3-carboxamide (prepared as described in Example 9) and 50.0 ml of N,N-dimethylacetamide dimethyl acetal are heated at 120° C. for 2 hours. After cooling, the reaction mixture is evaporated in vacuo to give an oil. The oil is triturated with diethyl ether to separate a yellow solid. The solid is collected by filtration, washed with ether, air dried, then dried in vacuo to give 12.37 g of the desired product as a tan solid, mp 124°–127° C.

The above-mentioned patents and publications are incorporated herein by reference.

Many variations of the present invention will suggest themselves to those skilled in this art in light of the above detailed description. All such obvious modifications are within the full intended scope of the appended claims.

We claim:

1. A compound of the formula:

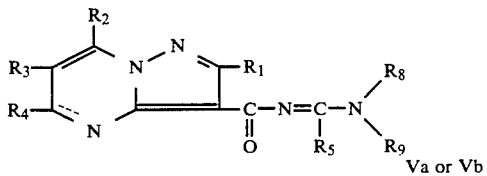

Va or Vb wherein --- may represent the presence of a double bond between the $N^4$ and $C^5$ position, Va, or the absence of a double bond between the $N^4$ and $C^5$ position and a hydrogen atom bonded to the $N^4$ position, Vb; $R_1$, $R_3$, $R_4$ and $R_5$ may be the same or different and are hydrogen or $C_1$ to $C_3$ alkyl; $R_2$ is

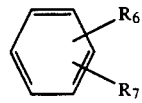

where $R_6$ and $R_7$ may be the same or different and are hydrogen, halogen, $C_1$ to $C_3$ alkyl or trifluoromethyl; $R_8$ and $R_9$ may be the same or different and are $C_1$ to $C_3$ alkyl, and where halogen is chlorine, bromine or fluorine; or a pharmaceutically-acceptable salt thereof.

2. A compound of the formula:

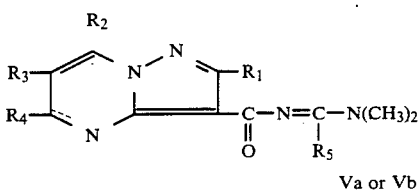

Va or Vb wherein --- may represent the presence of a double bond between the $N^4$ and $C^5$ position, Va, or the absence of a double bond between the $N^4$ and $C^5$ position and a hydrogen atom bonded to the $N^4$ position, Vb; $R_1$, $R_3$, $R_4$ and $R_5$ may be the same or different and are hydrogen or $C_1$ to $C_3$ alkyl; and $R_2$ is

where $R_6$ and $R_7$ may be the same or different and are hydrogen, halogen, $C_1$ to $C_3$ alkyl or trifluoromethyl; and where halogen is chlorine, bromine or fluorine; or a pharmaceutically acceptable salt thereof.

3. A compound as defined in claim 1, which is N-((dimethylamino)methylene)-7-phenylpyrazolo(1,5-a)pyrimidine-3-carboxamide.

4. A compound as defined in claim 1, which is N-((dimethylamino)methylene)-2-methyl-7-(3-(trifluoromethyl)phenyl)pyrazolo(1,5-a)pyrimidine-3-carboxamide.

5. A compound as defined in claim 1, which is N-((dimethylamino)methylene)-7-(3-methylphenyl)pyrazolo(1,5-a)pyrimidine-3-carboxamide.

6. A compound as defined in claim 1, which is N-((dimethylamino)methylene)-7-(3-(trifluoromethyl)phenyl)pyrazolo(1,5-a)pyrimidine-3-carboxamide.

7. A compound as defined in claim 1, which is N-((dimethylamino)methylene)-2-methyl-7-phenyl-pyrazolo(1,5-a)pyrimidine-3-carboxamide.

8. A compound as defined in claim 1, which is N-((dimethylamino)methylene)-2,5-dimethyl-7-phenyl-pyrazolo(1,5-a)pyrimidine-3-carboxamide.

9. A compound as defined in claim 1, which is N-((dimethylamino)methylene)-4,5-dihydro-7-(3-trifluoromethyl)phenyl)pyrazolo(1,5-a)pyrimidine-3-carboxamide.

* * * * *